(12) United States Patent
Xiangwu et al.

(10) Patent No.: US 7,082,831 B2
(45) Date of Patent: Aug. 1, 2006

(54) MEASUREMENT OF BASE AND SUBGRADE LAYER STIFFNESS USING BENDER ELEMENT TECHNIQUE

(76) Inventors: Zeng Xiangwu, 36110 South Huntington Dr., Solon, OH (US) 44139; Figueroa J. Ludwig, Dept of Civil Engineering, 136 Stocker Center, Ohio University, Athens, OH (US) 46701

( * ) Notice: Subject to any disclaimer, the term of this patent is extended or adjusted under 35 U.S.C. 154(b) by 156 days.

(21) Appl. No.: 10/844,891

(22) Filed: May 13, 2004

(65) Prior Publication Data
US 2004/0226380 A1 Nov. 18, 2004

Related U.S. Application Data

(60) Provisional application No. 60/470,019, filed on May 13, 2003.

(51) Int. Cl.
*G01N 29/07* (2006.01)
(52) U.S. Cl. ........................................... 73/594
(58) Field of Classification Search ................. 73/594, 73/597; 367/27; 181/111, 112
See application file for complete search history.

(56) References Cited

U.S. PATENT DOCUMENTS

| | | | |
|---|---|---|---|
| 5,177,709 A * | 1/1993 | Baziw | 367/38 |
| 5,432,305 A * | 7/1995 | Nelson | 181/101 |
| 6,386,044 B1 | 5/2002 | Weinmann | |
| 6,488,117 B1 * | 12/2002 | Owen | 181/121 |

* cited by examiner

*Primary Examiner*—John E. Chapman
(74) *Attorney, Agent, or Firm*—Howard M. Cohn

(57) ABSTRACT

The present invention relates to a device and method for measuring the stiffness of base and subgrade layers of soil. The device is a penetrometer comprising first and second spaced apart cone penetrometer shafts. A first of the cone penetrometer shafts is fitted with a set of at least two vertically spaced apart piezoelectric transmitters for wave transmission. The second cone penetrometer shaft is fitted with a set of at least two vertically spaced apart piezoelectric receivers for wave receiving. A trigger device is provided for triggering shear and primary waves from each piezoelectric transmitter to propagate through the soil. A capture device is provided for capturing the shear and primary waves from each of the piezoelectric receivers. A calculating device is provided for calculating soil stiffness from the measured shear and primary wave velocities.

19 Claims, 3 Drawing Sheets

CBR TEST RESULTS ON DELAWARE CLAY

CBR TEST RESULTS ON COARSE GRAINED SAND

CBR TEST RESULTS ON NEVADA SAND

MEASUREMENT OF BASE AND SUBGRADE LAYER STIFFNESS USING BENDER ELEMENT TECHNIQUE

CROSS-REFERENCE TO RELATED APPLICATIONS

This application claims the benefit of U.S. Provisional Patent Application No. 60/470,019 filed on May 13, 2003 which is incorporated herein by reference.

FIELD OF THE INVENTION

The present invention relates to the measurement of subgrade soil stiffness or resilient modulus, and more specifically to an apparatus and a method for measuring these parameters.

BACKGROUND OF THE INVENTION

The load bearing capacity of the soil supporting highways, airfield runways and other pavement systems is of immense importance to the integrity of the pavement. This load-bearing capacity, or soil stiffness, changes from time to time and can vary from place to place within a given area.

Soil stiffness is the degree of resistance to deformation upon loading. The extent and time-dependence of, and the degree of recovery from, deformation is primarily dependent upon the soil's properties, existing stress conditions, and the stress history. Soil properties in turn are determined by a variety of complex interrelated factors, including composition particle size and particle-size distribution, weight-volume relationships, and in-situ stresses.

The stability or load-bearing capacity (capability) of the pavement of airport runways, highways and other pavement systems is determined in significant part by the load-bearing capacity of the underlying subpavement) earth or soil, which may deteriorate over time due to environmental and stress influences on soil properties. For instance, changes in soil load-bearing conditions due to changes in moisture content and/or repeated loading over time are well recognized in engineering fields. In addition, certain pavement systems such as runways and highways typically endure repeated severe loadings on a daily basis.

The proper determination of existing bearing-load capacities of soil-supported pavement systems requires that the existing soil conditions be defined and evaluated. Conventional soil-structure modeling is based on the results of laboratory testing of individual localized soil samples, as in the case of the well-known California Bearing Ratio, or CBR, laboratory test. However, tests such as the CBR are severely disadvantaged because the test conditions and the soil sample (specimen) are not representative of in-situ conditions. Absent are (a) in-situ overburden stress, (b) in-situ soil interactions, and the like. Further, many if not most soil samples have been disturbed to some degree during sampling and handling. A true composite soil stiffness determination can only be determined using actual stiffness data of in-situ soil conditions at varying depths (varying subgrade conditions). In addition, while soil samples from individual lifts of soil placement can be obtained with relative ease before and/or during construction of the pavement system, thereafter the overlying structure generally precludes sampling of the supporting soil by nondestructive methods.

Another known method for determining composite soil stiffness is the use of plate bearing tests on the surface of soil layers.

As mentioned herein above, the current most widely used way to determine soil stiffness is by using the California Bearing Ratio (CBR) test on soil samples that are prepared in the laboratory, the objective being to calculate with the stiffness, or resilient modulus of soils, $M_R$, using generally accepted empirical expressions. An example of such an expression is the one recommended by American Association of State Highway and Transportation Officials (AASHTO):

$$M_R = 10,340 CBR (\text{kPa}) \tag{1}$$

The limitations of the CBR are discussed hereinabove. In summary they derive from that fact that the soil specimens of base, subbase, or subgrade layers are prepared in the laboratory using compaction procedures that are different from what the soils are subjected to in the field. Therefore, laboratory specimens may have stiffnesses that are different from the soils compacted in the field. Also, the CBR test does not provide the information needed by engineers to determine whether the stiffness of subgrade, subbase, and base soils of a pavement under construction in the field meets the design requirement, and for an existing pavement where the subgrade, subbase, and the base soils have gone through years of weather cycles and traffic load applications, the CBR test by itself cannot provide a realistic or representative measurement of soil stiffness. Therefore, there is the need to develop an in-situ, non-destructive, accurate and economical method for the measurement of stiffness of soils for pavement engineering applications.

Generally, soil stiffness determinations require (a) the application of a predetermined surface force and (b) the measurement of the resultant deflection or vertical deformation of the soil. Apparatus for applying a predetermined surface force are well known. Apparatus for measuring resultant deflection at the surface are also known. The challenge is the instrumentation and methodology needed to obtain actual stiffness data of in-situ soil conditions at varying depths to obtain the data necessary for the definition and evaluation of existing soil conditions, and then to properly determine existing bearing-load capacities of the overlying pavement system.

The most direct method of measuring composite and individual soil layer stiffness and deflections is through the use of a multi-depth deflectometer ("MDD"). U.S. Pat. No. 6,386,044 to Weinmann is an example of an MMD designed to be installed in a borehole for long periods during which data on soil layer displacements cane be gathered and stored for analysis.

SUMMARY OF THE INVENTION

The present invention is a device for measuring the stiffness of base and subgrade layers of soil. The invention comprises a pair of parallel spaced apart cone penetrometers. One of the cone penetrometers of the pair of spaced apart cone penetrators is fitted with at least two vertically spaced apart piezoelectric transmitters for shear and primary waves transmission. The other cone penetrators of the pair of spaced apart cone penetrators is fitted with at least two vertically spaced apart piezoelectric receivers for wave receiving. Wave generator means are provided for triggering shear and primary waves from each piezoelectric transmitter. The waves propagate through the soil to the piezoelectric receivers. Recording oscilloscope means are provided for capturing the shear and primary waves from each of the piezoelectric receivers. Soil stiffness is computed from the measured shear and primary wave velocities by means of the mathematical relationship between shear wave velocity, shear modulus, primary wave velocity, constrained modulus, and soil stiffness.

In a first embodiment of the invention, the at least two vertically spaced apart piezoelectric transmitters and the at least two vertically spaced apart piezoelectric receivers are disposed so as to project radially outward from the respective cone penetrometers of the pair of spaced apart cone penetrometers such that the radially projecting vertically spaced apart piezoelectric transmitters and the radially projecting at least two vertically spaced apart piezoelectric receivers project radially toward one another. The soil stiffness parameter is calculated from the measured shear and primary wave velocities according to a mathematical relationship between shear wave velocity, shear modulus, primary wave velocity, constrained modulus, and soil stiffness.

In a second embodiment of the invention, the at least two vertically spaced apart piezoelectric transmitters and the at least two vertically spaced apart piezoelectric receivers are disposed so as to project radially outward from the respective cone penetrometers of the pair of spaced apart cone penetrometers such that the set of at least two projecting vertically spaced apart piezoelectric transmitters and the set of at least two projecting vertically spaced apart piezoelectric receivers project radially toward one another, and flat metal webs which also project radially outward from the spaced apart penetrometers are used to protect the respective piezoelectric elements during soil insertion and removal.

In a third embodiment of the invention, the at least two vertically spaced apart piezoelectric transmitters and the at least two vertically spaced apart piezoelectric receivers are designed so as to be cylindrical in shape, having more or less the same diameter as the respective penetrometers, and concentric with the respective penetrometers.

Further, according to the invention, there is disclosed a method of measuring the stiffness of base and subgrade layers of soil. The method comprises the steps of: affixing together a pair of spaced apart cone penetrometers; fitting one of the cone penetrometers with a set of at least two vertically spaced apart piezoelectric transmitters for wave transmission through soil; fitting the second cone penetrometer with a set of at least two vertically spaced apart piezoelectric receivers for receiving the waves transmitted through the soil by the piezoelectric transmitters on the first cone penetrometer; pushing the pair of spaced apart and affixed together penetrometers into a layer of soil; triggering the transmission of shear and primary waves from the set of at least two piezoelectric transmitters; receiving the transmitted shear and primary waves with the set of at least two piezoelectric receivers; determining the travel time of shear and primary waves from the set of at least two piezoelectric transmitters to the set of at least two piezoelectric receivers; and calculating the soil stiffness on the basis of the travel time of the shear and primary waves and the application of a mathematical relationship between shear wave velocity, shear modulus, primary wave velocity, constrained modulus, and soil stiffness.

DEFINITIONS

CBR=California Bearing Ratio
$D_{10}$=particle size of soil with 10 percent finer particle size
$D_{30}$=particle size of soil with 30 percent finer
$D_{60}$=particle size of soil with 60 percent finer
E=Young's modulus of soil
$G_{max}$=elastic shear modulus of soil
L=distance between transmitter and receiver
$M_R$=resilient modulus
$t_s$=travel time of shear wave
$v_s$=shear wave velocity
$t_p$=travel time of primary wave
$v_p$=primary wave velocity
$\gamma_{dmax}$=maximum dry unit weight of soil (nt/m$^3$)
$\gamma_{dmin}$=minimum dry unit weight of soil (nt/m$^3$)
$\mu$=Poisson's ratio
$\rho$=mass density of soil
$\rho_{dry}$=dry mass density of soil The structure, operation, and advantages of the present preferred embodiment of the invention will become further apparent upon consideration of the following description taken in conjunction with the accompanying drawings, wherein:

DESCRIPTIONS OF THE PREFERRED EMBODIMENTS

Figure 1A:
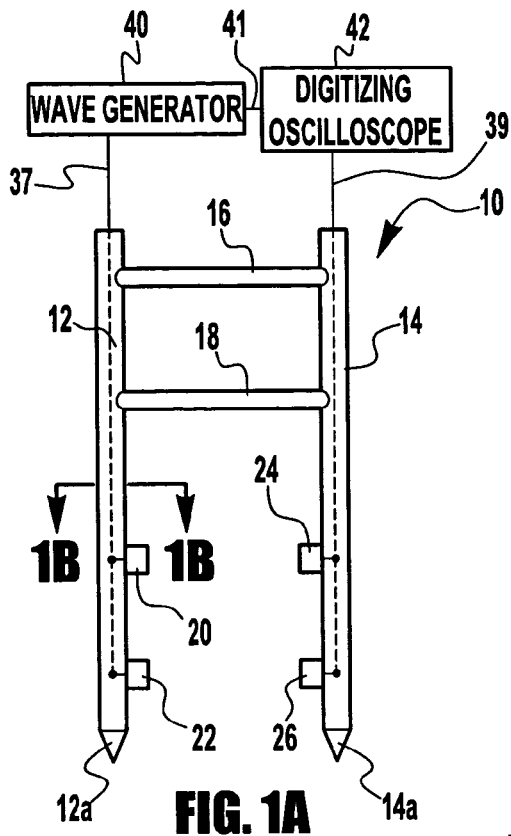
FIG. 1A illustrates the bender cone penetrometer of the present invention.

The present invention can measure the stiffness of base and subgrade layers quickly and accurately. Its operation is based upon the bender element technique. It is applicable to a wide variety of soil types, and the data have good repeatability. The Young's modulus derived from tests of this invention, especially with the pair of bender elements near the surface, agrees well with the resilient modulus derived from the aforementioned CBR tests. Since the present invention can be used on existing pavements and pavements under construction in the field, it offers a fast, accurate and low cost way to measure base and subgrade stiffness.

The experimental technique used to measure small-strain shear modulus of soil takes advantage of the bender element method, which has become a popular experiment way to measure shear wave velocity in soils in recent years. Bender elements are made of piezo-ceramic materials, in which an electrical excitation applied to a transmitter element leads to mechanical vibrations, which generates shear waves in the soil. Similarly in a wave receiver, a mechanical vibration of the element leads to an electrical output. Therefore, the velocity of a shear wave can be determined by measuring its travel time and the distance between the wave transmitter and receiver. Since the maximum shear strain generated by a bender element in the surrounding soil is on the order of 10–3%, the stress-strain relationship is well within the elastic range of soils. Similarly, extender elements can be used to measure wave velocity of primary waves. Bender elements and extender elements together are called piezoelectric sensors. This technique has been used by a number of researchers to measure the stiffness of sand and clay, in laboratory in recent years.

FIG. 1 shows one embodiment of a recently developed bender cone penetrometer 10. It consists of a pair of spaced apart, parallel cone penetrometer shafts 12,14 disposed about 20 centimeters apart and affixed in parallel relationship by cross members 16,18. Each cone penetrometer shafts 12,14 has a diameter of about 2.5 cm, and a length of about 1.5 meters. One end 12a, 12b of the cone penetrometers shafts 12,14 is cone shaped so that the pentrometer 10 can be more easily pressed into the ground. At least two vertically spaced apart, flat plate piezoelectric transmitters 20,22 affixed to the penetrometer element 14 project radially inward toward at least two corresponding, vertically spaced apart piezoelectric receiving elements 24,26, respectively, which also project radially outward from the penetrometer element 14 in the direction of the corresponding piezoelectric transmitters 20,22. In FIG. 1, the piezoelectric sources or transmitters 20,22 and the piezoelectric receiving elements 24,26 comprise a set of four piezoelectric elements. Throughout this disclosure, a total of four piezoelectric elements will be referred to, but it is within the scope of the present invention to incorporate more than four piezoelectric units to obtain more might precise measurements.

Figure 1B:
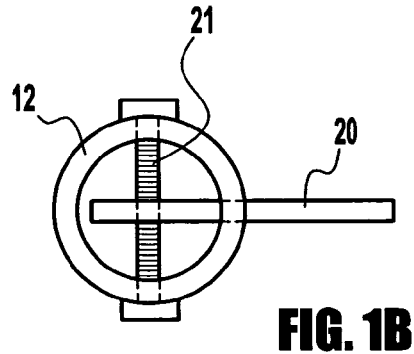
FIG. 1B is taken along line 1B—1B illustrates a bender cone penetrometer with two pairs of wave transmitters and receivers t.

FIG. 1B is an enlarged, cross-sectional view of one of the cone penetrometer shaft 12, showing the disposition method of attachment of the flat piezoelectric elements, such as piezoelectric transmitter 20, projecting radially outward from it. In the present embodiment, an attachment method such as a bolt 21 can extend through the penetrometer shafts to affix the flat piezoelectric elements in place.

Figure 1C:
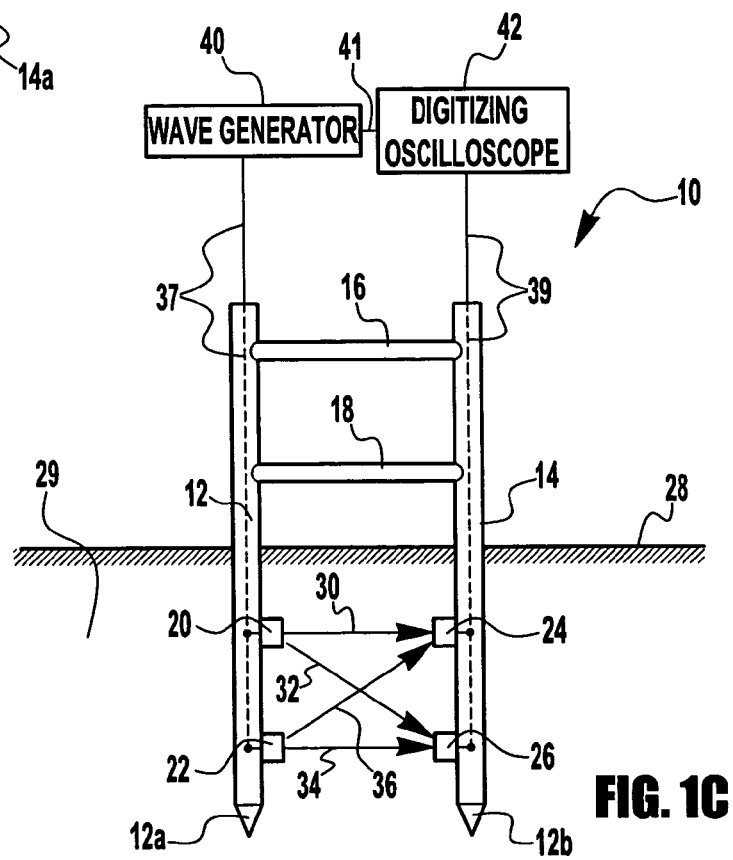
FIG. 1C illustrates the complete test setup during a test in progress.

FIG. 1C shows the cone penetrometer 10 of FIG. 1 with the ends 12a, 14a of the penetrometer shafts 12 and 14, respectively, disposed below the surface 28 of soil 29 whose stiffness is being measured. Shear and primary wave signals 30,32 are transmitted from the piezoelectric transmitter 20 to the piezoelectric receiving elements 24,26. Likewise, shear and primary wave signals 34,36 are transmitted from piezoelectric source or transmitter 22 to piezoelectric receivers 26,24.

Wave generator or signal generator means 40 are provided for triggering shear and primary waves from each piezoelectric transmitter 20,22. More specifically, the shear and primary waves that propagate from the piezoelectric transmitters 20, 22 are triggered by an electrical wave signal from the wave generator or signal generator 40. The wave generator or signal generator 40 is synchronized with a digitizing oscilloscope means 42, with which it communicates by connector line 41. The recording or digitizing oscilloscope means 42 are provided for capturing the shear and primary waves from each of the piezoelectric receivers 24,26. More specifically, wires 37,39 communicate respectively, between the wave generator 40 and the transmitters 20,22 and the digital recording oscilloscope means 42 and the receivers 24,26 which capture the transmitted shear and primary wave signals. Electrical outputs produced by the piezoelectric receivers 24,26 are recorded by the digitizing oscilloscope 42 which also records the waves from the wave generator 40. The travel time of the shear and primary waves from the piezoelectric transmitters 20,22 to respective receivers 24,26 can be determined on the basis of the oscilloscope's recorded travel time of the shear and primary waves from each piezoelectric transmitter to each piezoelectric receiver in conjunction with the distance between the radially projecting transmitters 20,22 and the radially projecting receivers 24,26 by way of the pathways 30,32,34,36 indicated in FIG. 1C. Then, the soil stiffness parameter can be calculated on the basis of the mathematical relationship between shear wave velocity, shear modulus, $G_{max}$, primary wave velocity, constrained modulus, and soil stiffness, as set forth herein below.

Because of the unique setup of the piezoelectric transmitters 20,22 and piezoelectric receivers 24,26, small-strain shear modulus on four shear planes can be measured simultaneously. From the travel time of shear wave between the upper bender transmitter 20 and upper bender receiver 24, the shear modulus near the surface 28 of the soil layer 29 can be determined. Similarly, $G_{max}$ near the bottom of the penetrometer 10 can be determined by monitoring the lower bender transmitter 22 and the lower bender receiver 26. At the same time, when the shear wave generated by the upper bender transmitter 20 is received by the lower bender receiver 26, the shear modulus on this inclined shear plane can be derived. Similarly, based on the wave velocity determined between the lower transmitter 22 and the upper receiver 20, the shear modulus on the corresponding shear plane can be derived and used to calculate the soil stiffness. It is therefore possible, in a single test setup, to measure shear modulus on four shear planes. Since the depth of the bender cone penetrometer shafts inside the soil layer 29 can be measured accurately by engraved marks (not shown in the FIGURES) on the penetrometer shafts 12 and 14, the depth location of the four planes can be accurately known. The average of the $G_{max}$ measured on the four planes provides a basis for deriving by computation and/or calculation the elastic stiffness of the soil layer over the depth of the penetrometer.

The piezoelectric elements 20,22,24,26 can be coated with epoxy or similar resistant coatings to make them water-tight and thereby allow their use in water saturated environments. Similarly, all the electrical connections within the penetrometer 10 can be made waterproof.

When the present invention is used in a setting where there is already located an existing pavement, two holes can be cored through the upper asphalt concrete or Portland cement concrete pavement layer and the penetrometer 10 can be pushed into the underlying soil layers to measure the stiffness of the underlying soil. Thus the penetrometer 10 can be used to check the mechanical properties of the sub layers of an existing pavement. A test can also be conducted quickly on the sublayers of a pavement under construction where the results can be displayed in a few minutes, allowing the cone penetrometer 10 of the present invention to be used to monitor compaction requirements.

To ensure that the first signals captured by the bender receivers 24,26 were indeed produced by shear waves, a technique similar to that used in seismic wave tests in the field has been adopted, where the poles of the electrical pulse that causes vibration are reversed. The received signals also showed a 180 degree phase change, thus confirming that the signals were generated by shear waves.

The soil stiffness parameter is calculated from the measured shear and primary wave velocities according to a mathematical relationship between shear wave velocity, shear modulus, primary wave velocity, constrained modulus, and soil stiffness. That is, supposing that the distance between a wave transmitter 20 or 22 and a corresponding wave receiver 24 or 26 is a length L, which is on the order of 20 cm, and the time for the wave to travel this distance is $t_s$, the average shear wave velocity is $$v_s = L/t_s \tag{2}$$

The elastic shear modulus of the soil $G_{max}$ would be $$G_{max} = \rho v_s^2 \tag{3}$$

in which $\rho$ is the density of the soil. The Young's modulus E, which is similar to the resilient modulus of soils in pavement design, can be calculated as:

$$E = 2(1+\mu)G_{max} \tag{4}$$

where $\mu$ is the Poisson's ratio, which has a typical value of 0.3 for dry soil.

When a pair of extender elements is used, wave velocity for primary waves and constrained modulus of a soil can be measured. Supposing the travel time for primary wave is $t_p$, the velocity of primary wave is $$v_p = L/t_p \tag{5}$$

The constrained modulus of the soil M is $$M = \rho v_p^2 \quad (6)$$

Combining the measurement of M and $G_{max}$, Poisson's ratio can be calculated as $$\mu = [(M/G_{max} - 2)/(2M/G_{max} - 2)]$$

Typical signals captured by a receiver are displayed on the recording oscilloscope 42, from which it is easy to accurately identify the transmission time, the arrival, and the travel time of the each acoustic signal. The elastic modulus along four wave paths 30, 32, 34 and 36 shown in FIG. 1C can be calculated using the abovementioned equations.

Experimental Results

Laboratory tests were conducted on three selected soils: a) Delaware clay from Delaware County, Ohio; b) a coarse-grained sand; and c) Nevada sand, using the bender cone penetrometer 10 to measure the elastic modulus. The resilient modulus of each of these soils was also measured using the CBR test for comparison purposes. The properties of all three soils are summarized in Table 1. It should be indicated that all soils are air dry.

sample was prepared, the bender cone penetrometer 10 was pushed into the soil slowly until the piezoelectric elements reached the specified depth (the upper group 20, 24 about 10 cm below soil surface, and the lower group 22, 26 about 16.5 cm below soil surface). Tests were then conducted to measure the shear and primary wave velocities by recording the average travel time of each wave path indicated in FIG. 1C. The cone penetrometer 10 can be inserted deeper in the soil for tests in the field, but in the laboratory, the depth was restricted by the height of the specially prepared mold (not shown). To ensure the repeatability of experimental data, each test was conducted on a second sample prepared according to the same procedures.

Test results on the three soils using the bender cone penetrometer 10 are summarized in Tables 2, 3, and 4, where the calculation of Young's modulus assumed a Poisson's ratio of 0.3 for all soils. Even though only air-dry soil samples were tested, the same equipment can be used below the ground water table if the piezoelectric elements and the

TABLE 1

A summary of properties of three soils used in the tests

| Soil | $D_{10}$ (mm) | $D_{30}$ (mm) | $D_{60}$ (mm) | Liquid limit | Plastic limit | Soil classification | $\gamma_{dmax}$ (kN/m³) | $\gamma_{dmin}$ (kN/m³) |
|---|---|---|---|---|---|---|---|---|
| Delaware clay | | | | 33.6% | 20.5% | Lean clay | 18.7* | |
| Nevada sand | 0.09 | 0.13 | 0.18 | | | Poorly graded sand | 17.3 | 13.9 |
| Coarse grained sand | 0.84 | 0.9 | 0.92 | | | Poorly graded sand | 16.5 | 14.0 |

*by modified Proctor

Tests were conducted on specimens of each soil compacted uniformly in five layers in a large steel mold. After a electrical connection are made waterproof, as described above.

TABLE 2

Test results on Delaware clay ($\rho_{dry}$ = 1557 kg/m³, $\mu$ = 0.3)

| | | $S_1 \to R_1$ (L = 5.46 cm) | | | $S_1 \to R_2$ (L = 7.51 cm) | | | $S_2 \to R_1$ (L = 7.58 cm) | | | $S_2 \to R_2$ (L = 5.54 cm) | | |
|---|---|---|---|---|---|---|---|---|---|---|---|---|---|
| | t (μs) | $G_{max}$ (MPa) | E (MPa) | t (μs) | $G_{max}$ (MPa) | E (MPa) | t (μs) | $G_{max}$ (MPa) | E (MPa) | t (μs) | $G_{max}$ (MPa) | E (MPa) |
| Test1 | 732 | 8.66 | 22.5 | 1388 | 4.56 | 11.9 | 1360 | 4.83 | 12.5 | 924 | 5.60 | 14.6 |
| Test2 | 684 | 9.92 | 25.7 | 1136 | 6.8 | 17.7 | 1292 | 5.36 | 13.9 | 948 | 5.32 | 13.8 |

TABLE 3

Test results on coarse-grained sand ($\rho_{dry}$ = 1620 kg/m³, $\mu$ = 0.3)

| | | $S_1 \to R_1$ (L = 5.46 cm) | | | $S_1 \to R_2$ (L = 7.51 cm) | | | $S_2 \to R_1$ (L = 7.58 cm) | | | $S_2 \to R_2$ (L = 5.54 cm) | | |
|---|---|---|---|---|---|---|---|---|---|---|---|---|---|
| | t (μs) | $G_{max}$ (MPa) | E (MPa) | t (μs) | $G_{max}$ (MPa) | E (MPa) | t (μs) | $G_{max}$ (MPa) | E (MPa) | t (μs) | $G_{max}$ (MPa) | E (MPa) |
| Test1 | 624 | 12.4 | 32.2 | 896 | 11.4 | 29.6 | 900 | 11.5 | 29.9 | 556 | 16.1 | 41.8 |
| Test2 | 616 | 12.7 | 33.1 | 852 | 12.6 | 32.7 | 860 | 12.6 | 32.7 | 560 | 15.9 | 41.2 |

TABLE 4

Test results on Nevada sand ($\rho_{dry}$ = 1612 kg/m³, $\mu$ = 0.3)

| | $S_1 \rightarrow R_1$ (L = 5.46 cm) | | | $S_1 \rightarrow R_2$ (L = 7.51 cm) | | | $S_2 \rightarrow R_1$ (L = 7.58 cm) | | | $S_2 \rightarrow R_2$ (L = 5.54 cm) | | |
|---|---|---|---|---|---|---|---|---|---|---|---|---|
| | t (µs) | $G_{max}$ (MPa) | E (MPa) | t (µs) | $G_{max}$ (MPa) | E (MPa) | t (µs) | $G_{max}$ (MPa) | E (MPa) | t (µs) | $G_{max}$ (MPa) | E (MPa) |
| Test1 | 540 | 16.5 | 42.8 | 804 | 14.1 | 36.6 | 774 | 15.5 | 40.2 | 450 | 24.4 | 63.5 |
| Test2 | 516 | 18.0 | 46.9 | 812 | 13.8 | 35.9 | 800 | 14.5 | 37.6 | 448 | 24.7 | 64.1 |

Figure 5:
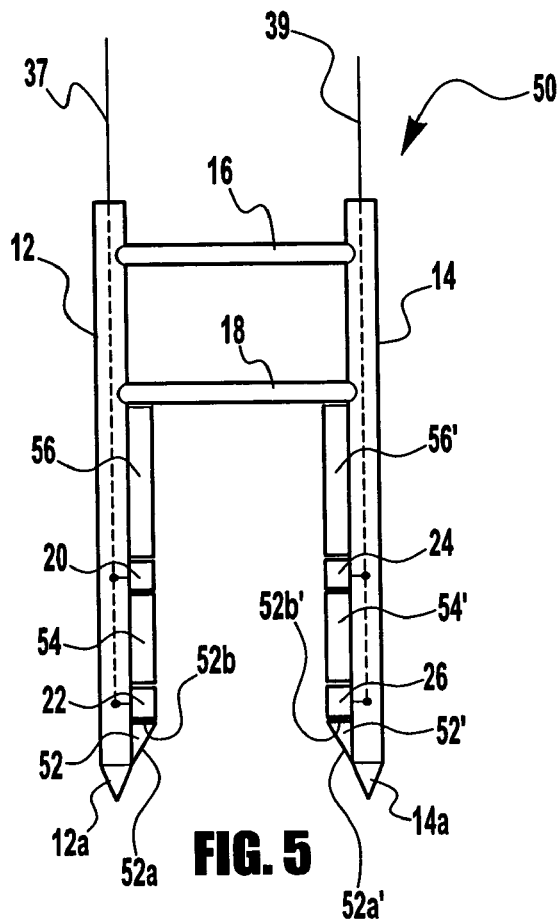
FIG. 5 shows a second embodiment of the invention.
Figure 6:
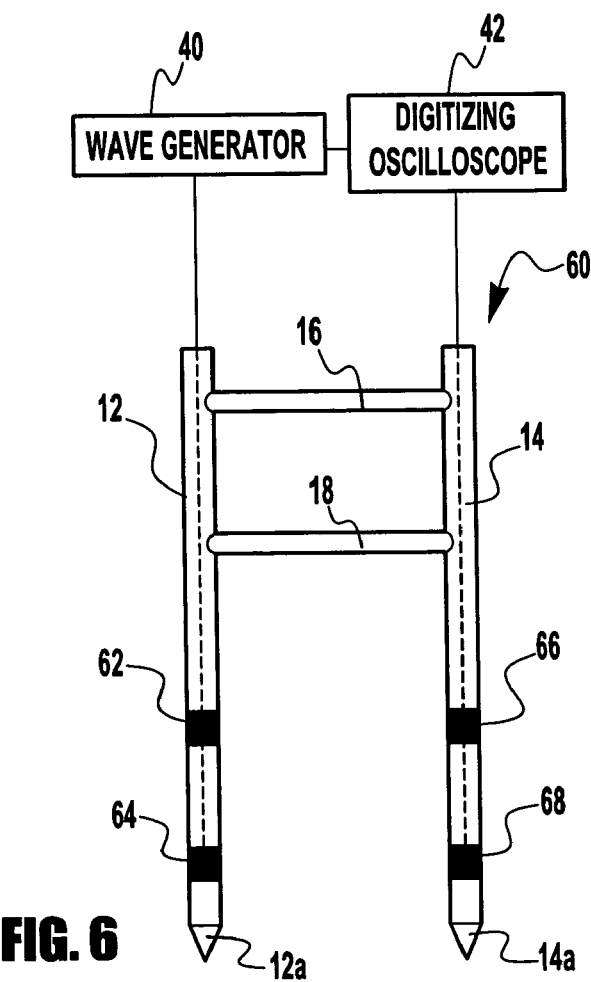
FIG. 6 shows a third embodiment of the invention.

To compare the results presented above from using the bender cone penetrometer 10 with the traditional CBR test-based method, two samples of each of the three soils were prepared in identical ways as for the bender element tests and CBR tests were conducted. Then, the resilient modulus, $M_R$, of the samples was calculated using equation (1). The CBR test results of the three soils are shown in FIGS. 5, 6, and 7, respectively, while the resilient modulus results are summarized in Table 5. For the CBR test on the Delaware clay, an overburden pressure equivalent to the effective stress at mid-depth of the bender cone penetrometer was used, since the dry clay appeared soft near the surface, without confining pressure.

TABLE 5

Summary of results of CBR tests

| | Delaware clay | | Coarse grained sand | | Nevada sand | |
|---|---|---|---|---|---|---|
| | CBR | $M_R$ (MPa) | CBR | $M_R$ (MPa) | CBR | $M_R$ (MPa) |
| Test1 | 2.46 | 25.4 | 3.97 | 41.0 | 4.18 | 43.2 |
| Test2 | 2.06 | 21.3 | 4.34 | 44.9 | 3.58 | 37.0 |

The soils used in the tests described above included a coarse grained sand, a fine grained sand, and a lean clay. Thus, this invention can be applied to a wide variety of soils that are typically used and found in the base and subgrade layers of pavements. As the data in Tables 2, 3 and 4 show, there seems to be a good repeatability of the data, an indication of good consistency and reliability of the technique. The general trend of the data from the three groups was the same, with the modulus measured by the upper pair of bender elements 20,24 high, the modulus measured by the two inclined paths slightly lower, and the modulus measured by the lower pair of bender elements 22,26 high again. This can be explained by the procedure of sample preparation and the effective stress state in the samples. Typically, near the top of the sample, the soil was compacted better. One the other hand, as the depth in the soil increases, the effective stress induced by the weight of soil above increases, thus the stiffness of the soil near the bottom starts to increase.

Figure 2:
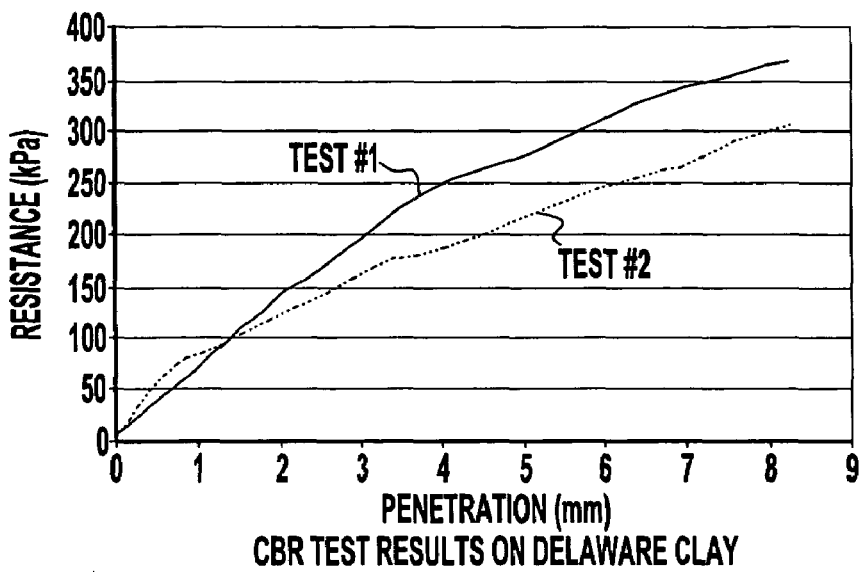
FIG. 2 shows CBR test results on Delaware clay.
Figure 3:
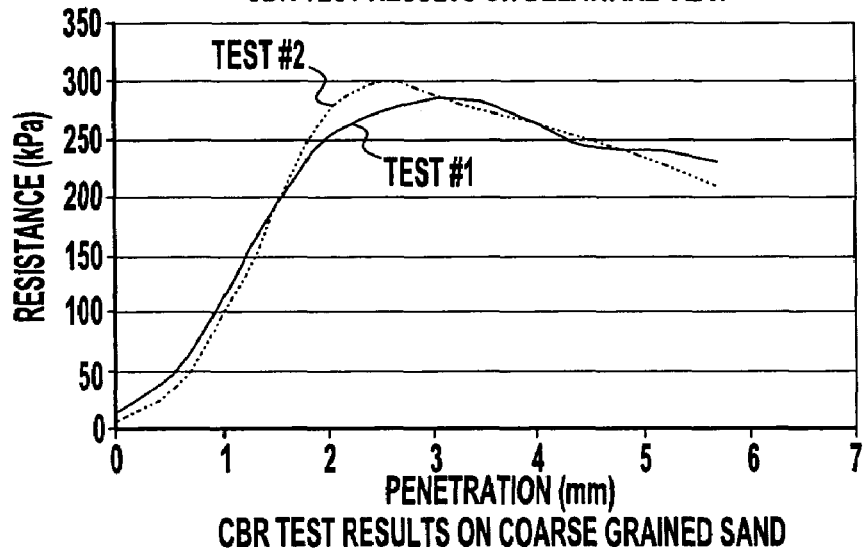
FIG. 3 CBR test results on coarse grained sand.
Figure 4:
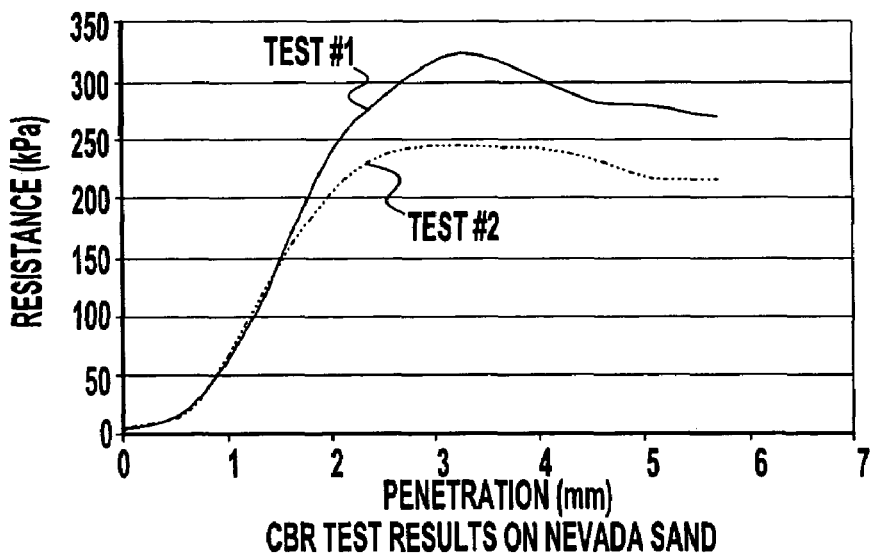
FIG. 4 CBR test results on Nevada sand.

Compared with the results of CBR tests as shown in FIGS. 2, 3 and 4, the tests using bender cone penetrometers seem to have better consistency and repeatability. The resilient modulus, $M_R$, calculated using the CBR numbers agrees well with the Young's modulus, E, measured by the top pair of bender elements on the cone penetrometer. This seems reasonable since the CBR value is mainly affected by the soil near the surface.

Additional Embodiments

The embodiment 10 of the present bender cone penetrometer shown in FIGS. 1A, 1B and 1C is a first embodiment of the present invention.

As should be apparent to those who are knowledgeable of the art, the projecting piezoelectric elements 20,22,24,26 causes them to be subjected to substantial stresses when the penetrometer shafts 12,14 are pushed into the soil whose stiffness is being measured. Accordingly, additional embodiments are provided to reduce any problem that might be encountered in pushing penetrometer shafts into the soil being measured.

FIG. 5 shows a second embodiment of a bender cone penetrometer 50 comprised of the same type of cone penetrometer shafts 12,14 having cross braces 16,18 and vertically spaced apart piezoelectric transmitters 20,22 and corresponding vertically spaced apart piezoelectric receivers 24,26. (NOTE: The same callout numbers are used to denote shafts that are substantially unchanged between the respective FIGURES.) FIG. 5 shows the addition of sets of flat metal webs 52,52' disposed forward (i.e., downward from, or vertically beneath) the lower piezoelectric transmitting and receiving elements 22,26. The flat web elements 52,52' have a generally triangular shape with the hypotenuse 52a, 52a' disposed to form a nearly straight line with the surface of the ends 12a and 14a, respectively. The upper side 52b and 52b' of the webs 52,52' extends parallel to the lower surface of the lower piezoelectric elements 22 and 26 and are at least the width of the piezoelectric elements as shown in FIG. 5. The web elements 52,52' are attached to the respective penetrometer shafts 12,14 so as to displace soil in front of the piezoelectric elements 22, 26 as the penetrometer 50 is pushed into the soil being tested. Additional rectangular shaped, flat web elements 54,54' are disposed between the respective upper and lower piezoelectric element sets 20, 22 and 24,26, the purpose being to protect the upper set of piezoelectric elements 20,24 from stresses associated with the insertion of penetrometer 50 into the soil. The width of the flat web elements 54,54' is at least the width of the upper and lower piezoelectric elements 20, 22 and 24,26. so as to help protect them prom the pressure of the soil during insertion into the ground. A pair of flat, rectangular shaped upper web elements 56,56' are also mounted to the respective penetrometer shafts 12,14 to protect the projecting piezoelectric elements 20, 22 and 24,26 by maintaining a clear pathway when the penetrometer 50 is removed from the soil being tested. As with the first embodiment 10, the second embodiment 50 has means 40 (not shown) for triggering shear and primary waves from each piezoelectric transmitter that propagate through the soil, means 42 for capturing said shear and primary waves with each of the piezoelectric receivers, and means for determining soil stiffness from the measured shear and primary wave velocities.

A third embodiment of a penetrometer 60 is displayed in FIG. 6. The vertically spaced apart piezoelectric transmitting elements 62,64 are concentric with the cone penetrometer shaft 12, and have more or less the same diameter as the respective penetrometers, thereby not projecting into the soil in a way that can expose them to adverse stresses during soil insertion of the embodiment 60. Likewise, the vertically spaced apart piezoelectric receiving elements 66,68 are concentric with the cone penetrometer shaft 14 and have more or less the same diameter as the cone penetrometer shaft 14, thereby not projecting into the soil in a way that can expose them to adverse stresses during soil insertion or removal of the embodiment 60. As with the first embodiment 10, the third embodiment 60 has an electrical wave signal generator means 40 for triggering shear and primary waves from each piezoelectric transmitter that propagate through the soil, means for capturing said shear and primary waves with each of the piezoelectric receivers, and means 42 for determining soil stiffness from the measured shear and primary wave velocities.

According to the invention, there is disclosed a method of measuring the stiffness of base and sub-grade layers of soil. The method comprises the steps of affixing together a pair of spaced apart parallel cone penetrometer shafts 12,14, fitting one of the cone penetrometer shafts 12 with a set of at least two vertically spaced apart piezoelectric transmitters 20,22, 62,64 for wave transmission through soil, fitting the second cone penetrometer shaft 14 with a set of at least two vertically spaced apart piezoelectric receivers 24,26, 66,68 for receiving the waves transmitted through the soil by the piezoelectric transmitters on the first cone penetrometer shaft 12, pushing the pair of spaced apart and affixed together penetrometer shafts into a layer of soil, triggering the transmission of shear and primary waves from the set of at least two piezoelectric transmitters 20,22, 62,64, receiving the transmitted shear and primary waves with the set of at least two piezoelectric receivers 24,26, 66,68, determining the travel time of a shear and primary waves from the set of at least two piezoelectric transmitters to the set of at least two piezoelectric receivers, and calculating the soil stiffness on the basis of the travel time of the shear and primary waves and the application of a mathematical relationship between shear wave velocity, shear modulus, primary wave velocity, constrained modulus, and soil stiffness in the digitizing oscilloscope or in a separate computer (not shown) attached to the digitizing oscilloscope. Within this method, the sets of at least two vertically spaced apart piezoelectric transmitters and the corresponding at least two vertically spaced apart piezoelectric receivers can be of the radially projecting sort described hereinabove, with or without flat metal web protectors, or the transmitters can be concentric with and have more or less the same diameter as the two parallel and spaced apart penetrometer shafts. The method of triggering shear and primary waves from the set of at least two piezoelectric transmitters is done by sending of an electrical waveform signal to the set of at least two piezoelectric transmitters. Likewise, the received signals from the at least two piezoelectric receivers is achieved by communicating the received shear and primary wave signals to a recording oscilloscope, wherein the shear and primary wave transmission time can be integrated with the shear and primary wave detection time such that the wave travel time can be calculated by the application of a mathematical relationship between shear wave velocity, shear modulus, primary wave velocity, constrained modulus, and soil stiffness.

Although the invention has been illustrated and described in detail in the drawings and foregoing description, the same is to be considered as illustrative and not restrictive in character—it being understood that only preferred embodiments have been shown and described, and that all changes and modifications that come within the spirit of the invention are desired to be protected. Undoubtedly, many other "variations" on the "themes" set forth hereinabove will occur to one having ordinary skill in the art to which the present invention most nearly pertains, and such variations are intended to be within the scope of the invention, as disclosed herein.

What is claimed is:

1. A device for measuring the stiffness of base and subgrade layers of soil, comprising:
   first and second spaced apart cone penetrometer shafts wherein:
      a first of the cone penetrometer shafts is fitted with a set of at least two vertically spaced apart, piezoelectric transmitters for wave transmission; and
      the second cone penetrometer shaft is fitted with a set of at least two vertically spaced apart piezoelectric receivers for wave receiving;
      means for triggering shear and primary waves from each piezoelectric transmitter that propagate through the soil;
      means for capturing the shear and primary waves from each of the piezoelectric receivers; and
      means for calculating soil stiffness from the measured shear and primary wave velocities.

2. The device of claim 1 wherein the set of at least two vertically spaced apart piezoelectric transmitters and the set of at least two vertically spaced apart piezoelectric receivers are each disposed so as to project radially outward from the respective cone penetrometer shafts of the pair of spaced apart cone penetrometer shafts such that the set of at least two protruding vertically spaced apart piezoelectric transmitters and the set of at least two protruding vertically spaced apart piezoelectric receivers project radially toward one another.

3. The device of claim 2 wherein the set of at least two vertically spaced apart piezoelectric transmitters and the set of at least two vertically spaced apart piezoelectric receivers that are disposed so as to project radially outward from the respective cone penetrometer shafts of the pair of spaced apart cone penetrometer shafts are protected by respective sets of flat metal webs.

4. The device of claim 1 wherein the means for triggering the shear and primary waves from each piezoelectric transmitter is a wave generator.

5. The device of claim 1 wherein the means for capturing the shear and primary waves from each piezoelectric receiver is a recording oscilloscope.

6. The device of claim 1 wherein the means for calculating the soil stiffness parameter from the measured shear and primary wave velocities is a computer that calculates a mathematical relationship between shear wave velocity, shear modulus, primary wave velocity, constrained modulus and soil stiffness.

7. A device for measuring the stiffness of base and subgrade layers of soil, comprising:
   a pair of spaced apart cone penetrometer shafts wherein:
      one of the cone penetrometer shafts of the apart of spaced apart cone penetrometer shafts is fitted with a set of at least two vertically spaced apart piezoelectric transmitters for wave transmission; and the other of the cone penetrometer shafts of the pair of waved apart cone penetrometer shafts is fitted with a set of at least two vertically spaced apart piezoelectric receivers for wave receiving;

means for triggering shear and primary waves from each piezoelectric transmitter that propagate through the soil;

means for capturing the shear and primary waves from each of the piezoelectric receiving;

means for calculating soil stiffness from the measured shear and primary wave velocities; and the set of at least two vertically spaced apart piezoelectric transmitters and the set of at least two vertically spaced apart piezoelectric receivers are designed so as to be cylindrical in shape, having more or less the same diameter as the respective penetrometer shafts, and concentric with the respective penetrometer shafts.

8. The device of claim 7 wherein the means for triggering the shear and primary waves from each piezoelectric transmitter is a wave generator.

9. The device of claim 7 wherein the means for capturing the shear and primary waves from each piezoelectric receiver is a recording oscilloscope.

10. The device of claim 7 wherein the means for calculating the soil stiffness parameter from the measured shear and primary wave velocities is a computer for calculating the mathematical relationship between shear wave velocity, shear modulus, primary wave velocity, constrained modulus, and soil stiffness.

11. The method of measuring the stiffness of base and subgrade layers of soil, comprising the steps of:

providing a penetrometer with a pair of spaced apart cone penetrometer shafts; fitting one of the cone penetrometer shafts with a set of at least two vertically spaced apart piezoelectric transmitters for wave transmission through soil;

fitting the second cone penetrometer shaft with a set of at least two vertically spaced apart bender receivers for receiving the waves transmitted through the soil by the piezoelectric transmitters on the first cone penetrometer shafts;

disposing the pair of spaced apart and affixed together penetrometer shafts into a layer of soil;

triggering the transmission of shear and primary waves from the set of at least two piezoelectric transmitters;

receiving the transmitted shear and primary waves with the set of at least two piezoelectric receivers;

determining the travel lime of a shear and primary wave from the set of at least two piezoelectric transmitters to the set of at least two piezoelectric receivers; and calculating the soil stiffness on the basis of the travel time of the shear and primary waves.

12. The method of claim 11 including the step of fitting one of the cone penetrometer shafts with a set of at least two vertically spaced apart piezoelectric transmitters such that the at least two piezoelectric transmitters project radially outward from the cone penetrometer.

13. The method of claim 11 including the step of fitting the second cone penetrometer shafts with a set of at least two vertically spaced apart piezoelectric receivers such that the at least two piezoelectric receivers project radially outward from the second cone penetrometer shaft.

14. The method of claim 11 including the step of fitting one of the cone penetrometer shafts with a set of at least two vertically spaced apart piezoelectric transmitters such that the at least two piezoelectric transmitters are concentric with and have more or less the same diameter as the cone penetrometer shafts.

15. The method of claim 11 including the step of fitting the second cone penetrometer shalt with a set of at least two vertically spaced apart piezoelectric receivers such that the at least two piezoelectric receivers are concentric with and have more or less the same diameter as the second cone penetrometer shaft.

16. The method of claim 11 including the step of triggering shear and primary waves from the set of at least two piezoelectric transmitters by sending of a waveform signal to the set of at least two piezoelectric transmitters.

17. The method of claim 11 including the step of sending shear and primary waves from the set of at least two piezoelectric receivers to a recording oscilloscope.

18. The method of claim 11 including the step of determining the travel time of the shear and primary waves from the set of at least two piezoelectric transmitters to the set of at least two piezoelectric receivers with a recording oscilloscope adapted to integrate the shear and primary wave transmission time with the shear and primary wave detection time.

19. The device of claim 11 including the step of calculating the soil stiffness by applying a mathematical relationship between shear wave velocity, shear modulus, primary wave velocity, constrained modulus, and soil stiffness.

* * * * *

UNITED STATES PATENT AND TRADEMARK OFFICE
CERTIFICATE OF CORRECTION

PATENT NO. : 7,082,831 B2  Page 1 of 1
APPLICATION NO. : 10/844891
DATED : August 1, 2006
INVENTOR(S) : Xiangwu et al.

It is certified that error appears in the above-identified patent and that said Letters Patent is hereby corrected as shown below:

Column 12,
Line 64, the word "apart" should be --pair--

Column 13,
Line 2, the word "waved" should be --spaced--

Column 14,
Line 1, the word "lime" should be --time--
Line 23, the word "shalt" should be --shaft--

Signed and Sealed this

Twelfth Day of December, 2006

JON W. DUDAS
*Director of the United States Patent and Trademark Office*